United States Patent
Wampler et al.

(10) Patent No.: US 10,479,755 B2
(45) Date of Patent: *Nov. 19, 2019

(54) TERMINALLY SELECTIVE METATHESIS OF POLYENES DERIVED FROM NATURAL OIL

(71) Applicant: Elevance Renewable Sciences, Inc., Woodridge, IL (US)

(72) Inventors: Keith M. Wampler, Woodridge, IL (US); Jane Uy, Woodridge, IL (US); Steven A. Cohen, Woodridge, IL (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/376,239

(22) Filed: Dec. 12, 2016

(65) Prior Publication Data
US 2017/0183289 A1    Jun. 29, 2017

Related U.S. Application Data

(63) Continuation of application No. 14/886,951, filed on Oct. 19, 2015, now Pat. No. 9,518,002.

(60) Provisional application No. 62/073,510, filed on Oct. 31, 2014.

(51) Int. Cl.
*C07C 67/475* (2006.01)
*C11C 3/14* (2006.01)
*C11C 1/04* (2006.01)

(52) U.S. Cl.
CPC .............. *C07C 67/475* (2013.01); *C11C 1/04* (2013.01); *C11C 3/14* (2013.01)

(58) Field of Classification Search
CPC ............ C07C 67/475; C11C 3/14; C11C 1/04
See application file for complete search history.

(56) References Cited

U.S. PATENT DOCUMENTS

| 7,534,917 | B1 * | 5/2009 | Ngo | C07C 51/353 |
|---|---|---|---|---|
| | | | | 562/590 |
| 2013/0035502 | A1 * | 2/2013 | Cohen | C10G 29/205 |
| | | | | 560/129 |
| 2013/0085288 | A1 * | 4/2013 | Snead | C11C 3/00 |
| | | | | 554/163 |

(Continued)

OTHER PUBLICATIONS

Van Dam, P.B., et al., Homogeneous catalytic metathesis of unsaturated fatty esters: New synthetic method for preparation of unsaturated mono- and dicarboxylic acids, 1974, The Journal of the American Oil Chemists' Society, vol. 51, pp. 389-392 (Year: 1974).*

(Continued)

*Primary Examiner* — Yate' K Cutliff
(74) *Attorney, Agent, or Firm* — Kilpatrick Townsend & Stockton LLP

(57) ABSTRACT

Methods of carrying out metathesis reactions of natural oil-derived polyenes (e.g., dienes and trienes), including functionalized polyenes, are generally disclosed herein. In some embodiments, the dienes or trienes contain a terminal carbon-carbon double bond, and the metathesis reaction is selective toward reaction of the terminal carbon-carbon double bonds in the polyene. Compounds made by such methods are also generally disclosed herein.

10 Claims, 1 Drawing Sheet

(56) References Cited

U.S. PATENT DOCUMENTS

2014/0121402 A1* 5/2014 Snead .................. C10L 1/02
560/190

OTHER PUBLICATIONS

Mol, J.C., Applications of olefin metathesis in the oleochemistry, 2002, Ring Opening Metathesis Polymerisation and Related Chemistry, Kluwer Academic Publishers, pp. 377-390 (Year: 2002).*

* cited by examiner

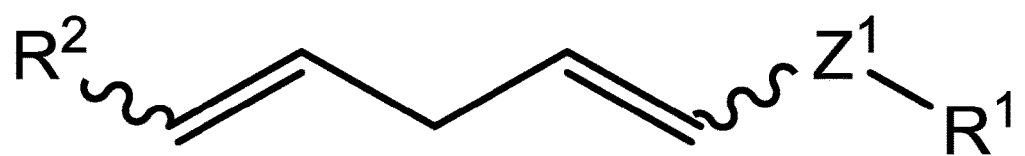

TERMINALLY SELECTIVE METATHESIS OF POLYENES DERIVED FROM NATURAL OIL

CROSS-REFERENCE TO RELATED APPLICATIONS

The present application is a continuation application of U.S. patent application Ser. No. 14/886,951, filed Oct. 19, 2015, which claims the benefit of priority of U.S. Provisional Application No. 62/073,510, filed Oct. 31, 2014, both of which are hereby incorporated by reference as though fully set forth herein in their entirety.

TECHNICAL FIELD

Methods of carrying out metathesis reactions of natural oil-derived polyenes (e.g., dienes and trienes), including functionalized polyenes, are generally disclosed herein. In some embodiments, the dienes or trienes contain a terminal carbon-carbon double bond, and the metathesis reaction is selective toward reaction of the terminal carbon-carbon double bonds in the polyene. Compounds made by such methods are also generally disclosed herein.

BACKGROUND

Metathesis is a catalytic reaction that involves the interchange of alkylidene units among compounds containing one or more double bonds (e.g., olefinic compounds) via the cleavage and formation of carbon-carbon double bonds. Metathesis may occur between two like molecules (often referred to as "self-metathesis") and/or it may occur between two different molecules (often referred to as "cross-metathesis"). Self-metathesis may be represented schematically as shown below in Equation (A):

$$R^a\text{—CH}=\text{CH—}R^b + R^a\text{—CH}=\text{CH—}R^b \leftrightarrow R^a\text{—CH}=\text{CH—}R^a + R^b\text{—CH}=\text{CH—}R^b, \quad (A)$$

wherein $R^a$ and $R^b$ are organic groups.

Cross-metathesis may be represented schematically as shown below in Equation (B):

$$R^a\text{—CH}=\text{CH—}R^b + R^c\text{—CH}=\text{CH—}R^d \leftrightarrow R^a\text{—CH}=\text{CH—}R^c + R^a\text{—CH}=\text{CH—}R^d + R^b\text{—CH}=\text{CH—}R^c + R^b\text{—CH}=\text{CH—}R^d, \quad (B)$$

wherein $R^a$, $R^b$, $R^c$, and $R^d$ are organic groups. Self-metathesis will also generally occur concurrently with cross-metathesis.

In the case of natural oil-derived polyenes, such as dienes or trienes, metathesis may occur at any one of the two or more carbon-carbon double bonds, typically separated by a methylene group. Without selectivity toward the terminal or internal double bonds, a metathesis of such compounds can lead to complex mixtures of a wide range of different compounds. In many cases, reaction at the internal carbon-carbon double bond is preferred, as that reaction may result in the creation of certain particularly stable co-products (such as 1,4-cyclohexadiene), which can end up acting as thermodynamic sinks. In such cases, it can be difficult to obtain reasonable yields of the longer-chain metathesis products that would be obtained if reaction at the terminal carbon-carbon double bonds were preferred.

Therefore, there is a continuing need to discover methods that can generate higher yields of products formed through reaction of the terminal carbon-carbon double bonds of polyenes.

SUMMARY

In a first aspect, the disclosure provides methods for forming a dimer by olefin metathesis, the method comprising:

providing a reactant composition comprising a compound of formula (Ia):

(Ia)

and a compound of formula (Ib):

(Ib)

and reacting the compound of formula (Ia) with the compound of formula (Ib) in the presence of a metathesis catalyst to form a product composition comprising a compound of formula (II):

(II)

wherein:

$Z^1$ is —(CH$_2$)$_7$—, or —CH$_2$—CH=CH—(CH$_2$)$_4$—, $R^1$ is an organic group; and $R^2$ is a hydrogen atom or an organic group;

provided that the compound of formula (Ia) is derived from a natural oil.

In a second aspect, the disclosure provides methods for forming a dimer by olefin metathesis, the method comprising: providing a reactant composition comprising methyl 9,12-tridecadienoate; and self-metathesizing the methyl 9,12-tridecadienoate in the presence of a metathesis catalyst to form a product composition comprising 1,24-dimethyl 9,12,15-tetracosatriendioate; provided that the methyl 9,12-tridecadienoate is derived from a natural oil.

In a third aspect, the disclosure provides methods for forming a dimer by olefin metathesis, the method comprising: providing a reactant composition comprising methyl 9,12-tridecadienoate and methyl 9-decenoate; and cross-metathesizing the methyl 9,12-tridecadienoate and the methyl 9-decenoate in the presence of a metathesis catalyst to form a product composition comprising 1,21-dimethyl 9,12-heneicosadiendioate; provided that the methyl 9,12-tridecadienoate or the methyl 9-decenoate is derived from a natural oil.

In a fourth aspect, the disclosure provides compounds formed by any of the methods of the first or second aspects.

Further aspects and embodiments are provided in the foregoing drawings, detailed description, and claims.

BRIEF DESCRIPTION OF THE DRAWINGS

The following drawings are provided for purposes of illustrating various embodiments of the compositions and methods disclosed herein. The drawings are provided for illustrative purposes only, and are not intended to describe any preferred compositions or preferred methods, or to serve as a source of any limitations on the scope of the claimed inventions.

The FIGURE shows a non-limiting example of a compound made according to certain embodiments disclosed herein, wherein: $Z^1$ is —$(CH_2)_7$—, or —$CH_2$—CH=CH—$(CH_2)_4$—; $R^1$ is an organic group; and $R^2$ is a hydrogen atom or an organic group.

DETAILED DESCRIPTION

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

As used herein, "reaction" and "reacting" refer to the conversion of a substance into a product, irrespective of reagents or mechanisms involved.

The term "group" refers to a linked collection of atoms or a single atom within a molecular entity, where a molecular entity is any constitutionally or isotopically distinct atom, molecule, ion, ion pair, radical, radical ion, complex, conformer etc., identifiable as a separately distinguishable entity. The description of a group as being "formed by" a particular chemical transformation does not imply that this chemical transformation is involved in making the molecular entity that includes the group.

As used herein, "mix" or "mixed" or "mixture" refers broadly to any combining of two or more compositions. The two or more compositions need not have the same physical state; thus, solids can be "mixed" with liquids, e.g., to form a slurry, suspension, or solution. Further, these terms do not require any degree of homogeneity or uniformity of composition. This, such "mixtures" can be homogeneous or heterogeneous, or can be uniform or non-uniform. Further, the terms do not require the use of any particular equipment to carry out the mixing, such as an industrial mixer.

As used herein, "metathesis catalyst" includes any catalyst or catalyst system that catalyzes an olefin metathesis reaction.

As used herein, "natural oil," "natural feedstock," or "natural oil feedstock" refer to oils derived from plants or animal sources. These terms include natural oil derivatives, unless otherwise indicated. The terms also include modified plant or animal sources (e.g., genetically modified plant or animal sources), unless indicated otherwise. Examples of natural oils include, but are not limited to, vegetable oils, algae oils, fish oils, animal fats, tall oils, derivatives of these oils, combinations of any of these oils, and the like. Representative non-limiting examples of vegetable oils include rapeseed oil (canola oil), coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil. Representative non-limiting examples of animal fats include lard, tallow, poultry fat, yellow grease, and fish oil. Tall oils are by-products of wood pulp manufacture. In some embodiments, the natural oil or natural oil feedstock comprises one or more unsaturated glycerides (e.g., unsaturated triglycerides). In some such embodiments, the natural oil feedstock comprises at least 50% by weight, or at least 60% by weight, or at least 70% by weight, or at least 80% by weight, or at least 90% by weight, or at least 95% by weight, or at least 97% by weight, or at least 99% by weight of one or more unsaturated triglycerides, based on the total weight of the natural oil feedstock.

As used herein, "natural oil derivatives" refers to the compounds or mixtures of compounds derived from a natural oil using any one or combination of methods known in the art. Such methods include but are not limited to saponification, fat splitting, transesterification, esterification, hydrogenation (partial, selective, or full), isomerization, oxidation, and reduction. Representative non-limiting examples of natural oil derivatives include gums, phospholipids, soapstock, acidulated soapstock, distillate or distillate sludge, fatty acids and fatty acid alkyl ester (e.g. non-limiting examples such as 2-ethylhexyl ester), hydroxy substituted variations thereof of the natural oil. For example, the natural oil derivative may be a fatty acid methyl ester ("FAME") derived from the glyceride of the natural oil. In some embodiments, a feedstock includes canola or soybean oil, as a non-limiting example, refined, bleached, and deodorized soybean oil (i.e., RBD soybean oil). Soybean oil typically comprises about 95% weight or greater (e.g., 99% weight or greater) triglycerides of fatty acids. Major fatty acids in the polyol esters of soybean oil include saturated fatty acids, as a non-limiting example, palmitic acid (hexadecanoic acid) and stearic acid (octadecanoic acid), and unsaturated fatty acids, as a non-limiting example, oleic acid (9-octadecenoic acid), linoleic acid (9,12-octadecadienoic acid), and linolenic acid (9,12,15-octadecatrienoic acid).

As used herein, "metathesize" or "metathesizing" refer to the reacting of a feedstock in the presence of a metathesis catalyst to form a "metathesized product" comprising new olefinic compounds, i.e., "metathesized" compounds. Metathesizing is not limited to any particular type of olefin metathesis, and may refer to cross-metathesis (i.e., co-metathesis), self-metathesis, ring-opening metathesis, ring-opening metathesis polymerizations ("ROMP"), ring-closing metathesis ("RCM"), and acyclic diene metathesis ("ADMET"). In some embodiments, metathesizing refers to reacting two triglycerides present in a natural feedstock (self-metathesis) in the presence of a metathesis catalyst, wherein each triglyceride has an unsaturated carbon-carbon double bond, thereby forming a new mixture of olefins and esters which may include a triglyceride dimer. Such triglyceride dimers may have more than one olefinic bond, thus higher oligomers also may form. Additionally, in some other embodiments, metathesizing may refer to reacting an olefin, such as ethylene, and a triglyceride in a natural feedstock having at least one unsaturated carbon-carbon double bond, thereby forming new olefinic molecules as well as new ester molecules (cross-metathesis).

As used herein, "alkyl" refers to a straight or branched chain saturated hydrocarbon having 1 to 30 carbon atoms, which may be optionally substituted, as herein further described, with multiple degrees of substitution being allowed. Examples of "alkyl," as used herein, include, but are not limited to, methyl, ethyl, n-propyl, isopropyl, isobutyl, n-butyl, sec-butyl, tert-butyl, isopentyl, n-pentyl, neopentyl, n-hexyl, and 2-ethylhexyl. The number carbon atoms in an alkyl group is represented by the phrase "$C_{x-y}$ alkyl," which refers to an alkyl group, as herein defined, containing from x to y, inclusive, carbon atoms. Thus, "$C_{1-6}$ alkyl" represents an alkyl chain having from 1 to 6 carbon atoms and, for example, includes, but is not limited to, methyl, ethyl, n-propyl, isopropyl, isobutyl, n-butyl, sec-butyl, tert-butyl, isopentyl, n-pentyl, neopentyl, and n-hexyl. In some instances, the "alkyl" group can be divalent, in which case the group can alternatively be referred to as an "alkylene" group. Also, in some instances, one or more of the carbon atoms in the alkyl or alkylene group can be replaced by a heteroatom (e.g., selected from nitrogen, oxygen, or sulfur, including N-oxides, sulfur oxides, and sulfur dioxides, where feasible), and is referred to as a "heteroalkyl" or "heteroalkylene" group. In some instances, one or more of the carbon atoms in the alkyl or alkylene group can be replaced by an oxygen atom, and is referred to as an "oxyalkyl" or "oxyalkylene" group.

As used herein, "alkenyl" refers to a straight or branched chain non-aromatic hydrocarbon having 2 to 30 carbon atoms and having one or more carbon-carbon double bonds, which may be optionally substituted, as herein further described, with multiple degrees of substitution being allowed. Examples of "alkenyl," as used herein, include, but are not limited to, ethenyl, 2-propenyl, 2-butenyl, and 3-butenyl. The number carbon atoms in an alkenyl group is represented by the phrase "$C_{x-y}$ alkenyl," which refers to an alkenyl group, as herein defined, containing from x to y, inclusive, carbon atoms. Thus, "$C_{2-6}$ alkenyl" represents an alkenyl chain having from 2 to 6 carbon atoms and, for example, includes, but is not limited to, ethenyl, 2-propenyl, 2-butenyl, and 3-butenyl. In some instances, the "alkenyl" group can be divalent, in which case the group can alternatively be referred to as an "alkenylene" group. Also, in some instances, one or more of the saturated carbon atoms in the alkenyl or alkenylene group can be replaced by a heteroatom (e.g., selected from nitrogen, oxygen, or sulfur, including N-oxides, sulfur oxides, and sulfur dioxides, where feasible), and is referred to as a "heteroalkenyl" or "heteroalkenylene" group. In some instances, one or more of the carbon atoms in the alkenyl or alkenylene group can be replaced by an oxygen atom, and is referred to as an "oxyalkenyl" or "oxyalkenylene" group.

As used herein, "halogen" or "halo" refers to fluorine, chlorine, bromine, and/or iodine. In some embodiments, the terms refer to fluorine and/or chlorine.

As used herein, "substituted" refers to substitution of one or more hydrogens of the designated moiety with the named substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week. As used herein, the phrases "substituted with one or more . . . " or "substituted one or more times . . . " refer to a number of substituents that equals from one to the maximum number of substituents possible based on the number of available bonding sites, provided that the above conditions of stability and chemical feasibility are met.

As used herein, "optionally" means that the subsequently described event(s) may or may not occur. In some embodiments, the optional event does not occur. In some other embodiments, the optional event does occur one or more times.

As used herein, "comprise" or "comprises" or "comprising" or "comprised of" refer to groups that are open, meaning that the group can include additional members in addition to those expressly recited. For example, the phrase, "comprises A" means that A must be present, but that other members can be present too. The terms "include," "have," and "composed of" and their grammatical variants have the same meaning. In contrast, "consist of" or "consists of" or "consisting of" refer to groups that are closed. For example, the phrase "consists of A" means that A and only A is present.

As used herein, "or" is to be given its broadest reasonable interpretation, and is not to be limited to an either/or construction. Thus, the phrase "comprising A or B" means that A can be present and not B, or that B is present and not A, or that A and B are both present. Further, if A, for example, defines a class that can have multiple members, e.g., $A_1$ and $A_2$, then one or more members of the class can be present concurrently.

As used herein, the various functional groups represented will be understood to have a point of attachment at the functional group having the hyphen or dash (-) or an asterisk (*). In other words, in the case of —$CH_2CH_2CH_3$, it will be understood that the point of attachment is the $CH_2$ group at the far left. If a group is recited without an asterisk or a dash, then the attachment point is indicated by the plain and ordinary meaning of the recited group.

As used herein, multi-atom bivalent species are to be read from left to right. For example, if the specification or claims recite A-D-E and D is defined as —OC(O)—, the resulting group with D replaced is: A-OC(O)-E and not A-C(O)O-E.

Other terms are defined in other portions of this description, even though not included in this subsection.

Methods of Dimer Formation

In certain aspects and embodiments, the disclosure provides methods for forming a dimer by olefin metathesis, the method comprising: providing a reactant composition comprising a compound of formula (Ia):

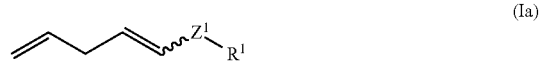

and a compound of formula (Ib):

and reacting the compound of formula (Ia) with the compound of formula (Ib) in the presence of a metathesis catalyst to form a product composition comprising a compound of formula (II):

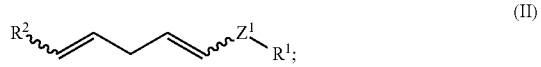

(II)

wherein:

$Z^1$ is —$(CH_2)_7$—, or —$CH_2$—CH=CH—$(CH_2)_4$—;

$R^1$ is an organic group; and $R^2$ is a hydrogen atom or an organic group. In some such embodiments, the compounds of formula (Ia) are derived from a natural oil (as described in further detail below). In some further embodiments, the compounds of formula (Ib) are derived from a natural oil.

In some embodiments of the aforementioned embodiments, $Z^1$ is —$(CH_2)_7$—. In some other such embodiments, $Z^1$ is —$CH_2$—CH=CH—$(CH_2)_4$—.

In some embodiments of any of the aforementioned embodiments, $R^1$ is methyl. In some other such embodiments, $R^1$ is a carboxylic acid group (—$CO_2H$), an ester group (—$CO_2R$), an amide group (—$CONH_2$, —CONHR, $CONR_2$), a carboxylate salt group ($COO^-$), an aldehyde group (—CHO), a ketone group (—C(=O)—R), an acyl halide group (—C(=O)X), a —$CH_2$—OH group, or a —CN group; where R is any organic group and X is a halogen atom. In some such embodiments, $R^1$ is a carboxylic acid group. In some other such embodiments, $R^1$ is an ester group. In some further such embodiments, $R^1$ is —C(=O)—O—($C_{1-12}$ alkyl), such as —C(=O)—O—$CH_3$ or —C(=O)—O—$CH_2$—$CH_3$. In some embodiments, $R^1$ is —C(=O)—O—$CH_3$.

In some embodiments of any of the aforementioned embodiments, $R^2$ is a hydrogen atom. In some other such embodiments, $R^2$ is an organic group. In some such embodiments, $R^2$ is $C_{1-12}$ alkyl or $C_{2-12}$ alkenyl. In some further such embodiments, $R^2$ is methyl, ethyl, propyl, butyl, pentyl, hexyl, heptyl, or hexyl. In some other such embodiments, $R^2$ is —$CH_2$—CH=CH—$(CH_2)_4$—$CH_3$, —$CH_2$—CH=CH—$CH_2$—$CH_3$, or —$CH_2$—CH=CH—$CH_2$—CH=CH—$CH_2$—$CH_3$. In some other such embodiments, $R^2$ is —$(CH_2)_7$—$R^3$, —$CH_2$—CH=CH—$(CH_2)_7$—$R^3$, or —$CH_2$—CH=CH—$CH_2$—CH=CH—$(CH_2)_7$—$R^3$, wherein $R^3$ is a carboxylic acid group, an ester group, an amide group, a carboxylate salt group, an aldehyde group, a ketone group, an acyl halide group, a —$CH_2$—OH group, or a —CN group. In some even further such embodiments, $R^2$ is —$(CH_2)_7$—$R^3$, and $R^3$ is —C(=O)—O—($C_{1-12}$ alkyl), such as —C(=O)—O—$CH_3$ or —C(=O)—O—$CH_2$—$CH_3$. In some even further embodiments, $R^2$ is —$(CH_2)_7$—C(=O)—O—$CH_3$. In some embodiments, $R^2$ is —$CH_2$—CH=CH—$(CH_2)_7$—$R^3$, and $R^3$ is —C(=O)—O—($C_{1-12}$ alkyl), such as —C(=O)—O—$CH_3$ or —C(=O)—O—$CH_2$—$CH_3$. In some further such embodiments, $R^2$ is —$CH_2$—CH=CH—$(CH_2)_7$—C(=O)—O—$CH_3$. In some embodiments, $R^2$ is —$CH_2$—CH=CH—$CH_2$—CH=CH—$(CH_2)_7$—$R^3$, and $R^3$ is —C(=O)—O—($C_{1-12}$ alkyl), such as —C(=O)—O—$CH_3$ or —C(=O)—O—$CH_2$—$CH_3$. In some further such embodiments, $R^2$ is —$CH_2$—CH=CH—$CH_2$—CH=CH—$(CH_2)_7$—C(=O)—O—$CH_3$.

In some embodiments of any of the aforementioned embodiments, the reaction is selective to metathesis occurring at the terminal carbon-carbon double bond of the compounds of formula (Ia) and/or the compounds of formula (Ib), meaning that the compounds of formula (II) are preferred relative to other possible metathesis products (e.g., other products where the reaction occurs at an internal carbon-carbon double bond).

In some embodiments, this selectivity can be stated in terms of the percent yield of the compound of formula (II). Thus, in some embodiments, the reacting step of the method generates the compound of formula (II) in a yield of at least 30%, or at least 40%, or at least 50%, or at least 60%, or at least 70%, or at least 80%, in the product composition.

In some other embodiments, it can be desirable to state the selectivity in terms of a selectivity percentage, which is the weight percent of the compound of formula (II) formed, based on the total weight of all metathesis products formed. In some embodiments, the selectivity is at least 60%, or at least 65%, or at least 70%, or at least 75%, or at least 80%, or at least 85%, or at least 90%.

The compounds of formula (II) can be further reacted to make other useful products. For example, such compounds can be hydrogenated to make certain saturated hydrocarbons or certain saturated difunctional compounds, e.g., saturated dibasic acids. For example, 1,24-dimethyl 9,12,15-tetracosatrienedioate can be hydrogenated to form 1,24-dimethyl tetracosanedioate. In some embodiments, this can be converted to a dibasic carboxylic acid (i.e., tetracosanedioic acid) by hydrolysis or by saponification followed by acidification. Such methods are well known in the art.

The hydrogenation can be carried by any suitable means. In certain embodiments, hydrogen gas is reacted with the unsaturated dibasic ester in the presence of a hydrogenation catalyst to form a saturated dibasic acid, for example, in a hydrogenation reactor.

Any suitable hydrogenation catalyst can be used. In some embodiments, the hydrogenation catalyst comprises nickel, copper, palladium, platinum, molybdenum, iron, ruthenium, osmium, rhodium, or iridium, individually or in any combinations thereof. Such catalysts may be heterogeneous or homogeneous. In some embodiments, the catalysts are supported nickel or sponge nickel type catalysts. In some embodiments, the hydrogenation catalyst comprises nickel that has been chemically reduced with hydrogen to an active state (i.e., reduced nickel) provided on a support. The support may comprise porous silica (e.g., kieselguhr, infusorial, diatomaceous, or siliceous earth) or alumina. The catalysts are characterized by a high nickel surface area per gram of nickel. Commercial examples of supported nickel hydrogenation catalysts include those available under the trade designations NYSOFACT, NYSOSEL, and NI 5248 D (from BASF Catalysts LLC, Iselin, N.J.). Additional supported nickel hydrogenation catalysts include those commercially available under the trade designations PRICAT Ni 62/15 P, PRICAT Ni 55/5, PPRICAT 9910, PRICAT 9920, PRICAT 9908, PRICAT 9936 (from Johnson Matthey Catalysts, Ward Hill, Mass.).

The supported nickel catalysts may be of the type described in U.S. Pat. Nos. 3,351,566, 6,846,772, European Patent Publication No. 0168091, and European Patent Publication No. 0167201, each of which are incorporated by reference herein in their entireties. Hydrogenation may be carried out in a batch or in a continuous process and may be partial hydrogenation or complete hydrogenation. In certain embodiments, the temperature ranges from about 50° C. to about 350° C., about 100° C. to about 300° C., about 150° C. to about 250° C., or about 100° C. to about 150° C. The desired temperature may vary, for example, with hydrogen gas pressure. Typically, a higher gas pressure will require a lower temperature. Hydrogen gas is pumped into the reaction vessel to achieve a desired pressure of $H_2$ gas. In certain embodiments, the $H_2$ gas pressure ranges from about 15 psig (1 barg) to about 3000 psig (204.1 barg), about 15 psig (1 barg) to about 90 psig (6.1 barg), or about 100 psig (6.8 barg) to about 500 psig (34 barg). As the gas pressure increases, more specialized high-pressure processing equipment may be required. In certain embodiments, the reaction conditions are "mild," wherein the temperature is approximately between approximately 50° C. and approximately 100° C. and the $H_2$ gas pressure is less than approximately 100 psig. In other embodiments, the temperature is between about 100° C. and about 150° C., and the pressure is between about 100 psig (6.8 barg) and about 500 psig (34 barg). When the desired degree of hydrogenation is reached, the reaction mass is cooled to the desired filtration temperature.

The amount of hydrogenation catalyst is typically selected in view of a number of factors including, for example, the type of hydrogenation catalyst used, the amount of hydrogenation catalyst used, the degree of unsaturation in the material to be hydrogenated, the desired rate of hydrogenation, the desired degree of hydrogenation (e.g., as measure by iodine value (IV)), the purity of the reagent, and the $H_2$ gas pressure. In some embodiments, the hydrogenation catalyst is used in an amount of about 10 percent by weight or less, for example, about 5 percent by weight or less or about 1 percent by weight or less.

Following the metathesis (described above) the resulting composition can contain various impurities. These impurities can be compounds that were made by various kinds of unproductive metathesis. Or, in some instances, the impurities may result from the presence of impurities in the starting compositions. In any event, it can, in some embodiments, be desirable to strip out and/or distill out these impurities. In some such embodiments, the stripping and/or distilling can occur after the metathesis, but before the hydrogenation. In some alternative embodiments, the stripping and/or distilling can occur after both the metathesis and the hydrogenation. These impurities may contain more esters than hydrocarbons (e.g., monobasic esters), as certain alkene impurities can be vented out of the reactor during the metathesis reaction, e.g., due to the lower relative boiling point of the alkene impurities. Of course, in some instances, these alkene impurities may stay in the reactor long enough to involve themselves in certain metathesis reactions, thereby generating other impurities (e.g., an additional alkene impurity and an additional ester impurity). Paraffin impurities can also be present, which can be removed by the stripping and/or distilling, for example, after hydrogenation.

In some embodiments, the stripping may lead to the removal of certain amounts of the compounds of formula (Ia) and the compounds of formula (Ib). In some such embodiments, these stripped out reactants can be collected and reused for further metathesis reactions.

In certain embodiments, the disclosure provides methods for forming a dimer by olefin metathesis, the method comprising: providing a reactant composition comprising methyl 9,12-tridecadienoate; and self-metathesizing the methyl 9,12-tridecadienoate in the presence of a metathesis catalyst to form a product composition comprising 1,24-dimethyl 9,12,15-tetracosatriendioate; provided that the methyl 9,12-tridecadienoate is derived from a natural oil. In some embodiments, the 1,24-dimethyl 9,12,15-tetracosatriendioate is further saturated to form 1,24-dimethyl tetracosanedioate. In some further embodiments, the saturated diester of converted to a saturated dibasic acid, e.g., by hydrolysis or saponification followed by acidification.

In certain embodiments, the disclosure provides methods for forming a dimer by olefin metathesis, the method comprising: providing a reactant composition comprising methyl 9,12-tridecadienoate and methyl 9-decenoate; and cross-metathesizing the methyl 9,12-tridecadienoate and the methyl 9-decenoate in the presence of a metathesis catalyst to form a product composition comprising 1,21-dimethyl 9,12-heneicosadiendioate; provided that the methyl 9,12-tridecadienoate or the methyl 9-decenoate is derived from a natural oil. In some embodiments, the 1,21-dimethyl 9,12-heneicosadiendioate is further saturated to form 1,21-dimethyl heneicosanedioate. In some further embodiments, the saturated diester of converted to a saturated dibasic acid, e.g., by hydrolysis or saponification followed by acidification.

Metathesis and Metathesis Catalysts

The aforementioned methods are carried out in the presence of a metathesis catalyst, which serves to catalyze the exchange of the alkylidene groups between the two olefinic reactants.

The metathesis process can be conducted under any conditions adequate to produce the desired metathesis products. For example, stoichiometry, atmosphere, solvent, temperature, and pressure can be selected by one skilled in the art to produce a desired product and to minimize undesirable byproducts. In some embodiments, the metathesis process may be conducted under an inert atmosphere. Similarly, in embodiments were a reagent is supplied as a gas, an inert gaseous diluent can be used in the gas stream. In such embodiments, the inert atmosphere or inert gaseous diluent typically is an inert gas, meaning that the gas does not interact with the metathesis catalyst to impede catalysis to a substantial degree. For example, non-limiting examples of inert gases include helium, neon, argon, and nitrogen, used individually or in with each other and other inert gases.

The rector design for the metathesis reaction can vary depending on a variety of factors, including, but not limited to, the scale of the reaction, the reaction conditions (heat, pressure, etc.), the identity of the catalyst, the identity of the materials being reacted in the reactor, and the nature of the reactants being employed. Suitable reactors can be designed by those of skill in the art, depending on the relevant factors, and incorporated into a refining process such, such as those disclosed herein.

The metathesis reactions disclosed in the aforementioned embodiments generally occur in the presence of one or more metathesis catalysts. Such methods can employ any suitable metathesis catalyst. The metathesis catalyst in this reaction may include any catalyst or catalyst system that catalyzes a metathesis reaction. Any known metathesis catalyst may be used, alone or in combination with one or more additional catalysts. Examples of metathesis catalysts and process conditions are described in US 2011/0160472, incorporated by reference herein in its entirety, except that in the event of any inconsistent disclosure or definition from the present specification, the disclosure or definition herein shall be deemed to prevail. A number of the metathesis catalysts described in US 2011/0160472 are presently available from Materia, Inc. (Pasadena, Calif.).

In some embodiments, the metathesis catalyst includes a Grubbs-type olefin metathesis catalyst and/or an entity derived therefrom. In some embodiments, the metathesis catalyst includes a first-generation Grubbs-type olefin metathesis catalyst and/or an entity derived therefrom. In some embodiments, the metathesis catalyst includes a second-generation Grubbs-type olefin metathesis catalyst and/or an entity derived therefrom. In some embodiments, the metathesis catalyst includes a first-generation Hoveyda-Grubbs-type olefin metathesis catalyst and/or an entity derived therefrom. In some embodiments, the metathesis catalyst includes a second-generation Hoveyda-Grubbs-type olefin metathesis catalyst and/or an entity derived therefrom. In some embodiments, the metathesis catalyst includes one or a plurality of the ruthenium carbene metathesis catalysts sold by Materia, Inc. of Pasadena, Calif. and/or one or more entities derived from such catalysts.

In some other embodiments, the metathesis catalyst includes a molybdenum and/or tungsten alkylidene complex and/or an entity derived from such a complex. In some embodiments, the metathesis catalyst includes a Schrock-type olefin metathesis catalyst and/or an entity derived therefrom. In some embodiments, the metathesis catalyst includes a high-oxidation-state alkylidene complex of molybdenum and/or an entity derived therefrom. In some embodiments, the metathesis catalyst includes a high-oxidation-state alkylidene complex of tungsten and/or an entity derived therefrom. In some embodiments, the metathesis catalyst includes molybdenum (VI). In some embodiments, the metathesis catalyst includes tungsten (VI). In some embodiments, the metathesis catalyst includes a molybdenum- and/or a tungsten-containing alkylidene complex of a type described in one or more of (a) Angew. Chem. Int. Ed. Engl., 2003, 42, 4592-4633; (b) Chem. Rev., 2002, 102, 145-179; and/or (c) Chem. Rev., 2009, 109, 3211-3226, each of which is incorporated by reference herein in its entirety, except that in the event of any inconsistent disclosure or definition from the present specification, the disclosure or definition herein shall be deemed to prevail. In some embodiments, suitable metathesis catalysis include those disclosed in one or more of the following references: PCT Publication No. WO 2014139679; U.S. Patent Application Publication Nos. 2012/0302710, 2011/0077421, 2011/0015430, 2008/0119678; Singh et al., Organometallics, vol. 26, p. 2528 (2007); Meek et al., Nature, vol. 456, pp. 933-37 (2008); Wampler et al., Organometallics, vol. 26, p. 6674 (2007); all of which are hereby incorporated by reference as though fully set forth herein. In some embodiments, such structures can be described as compounds of formula (III):

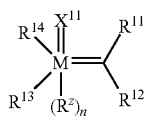

(III)

wherein:

$R^{11}$ and $R^{12}$ are independently a hydrogen atom or an organic group;

$R^{13}$ is an anionic ligand;

$R^{14}$ is an anionic ligand that comprises a nitrogen-containing ring system, where a nitrogen atom of the ring system is bond to M (e.g., 2,5-dimethylpyrrolide);

$R^z$ is a neutral ligand;

M is Mo or W;

$X^{11}$ is =O or =N—$R^{15}$, wherein $R^{15}$ is a hydrogen atom or an organic group; and n is 0 or 1;

wherein any two or more of the ligands on the metal can optionally combine to form a multidentate ligand.

In certain embodiments, the metathesis catalyst is dissolved in a solvent prior to conducting the metathesis reaction. In certain such embodiments, the solvent chosen may be selected to be substantially inert with respect to the metathesis catalyst. For example, substantially inert solvents include, without limitation: aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc. In some embodiments, the solvent comprises toluene.

In other embodiments, the metathesis catalyst is not dissolved in a solvent prior to conducting the metathesis reaction. The catalyst, instead, for example, can be slurried with the natural oil or unsaturated ester, where the natural oil or unsaturated ester is in a liquid state. Under these conditions, it is possible to eliminate the solvent (e.g., toluene) from the process and eliminate downstream olefin losses when separating the solvent. In other embodiments, the metathesis catalyst may be added in solid state form (and not slurried) to the natural oil or unsaturated ester (e.g., as an auger feed).

The metathesis reaction temperature may, in some instances, be a rate-controlling variable where the temperature is selected to provide a desired product at an acceptable rate. In certain embodiments, the metathesis reaction temperature is greater than −40° C., or greater than −20° C., or greater than 0° C., or greater than 10° C. In certain embodiments, the metathesis reaction temperature is less than 200° C., or less than 150° C., or less than 120° C. In some embodiments, the metathesis reaction temperature is between 0° C. and 150° C., or is between 10° C. and 120° C.

The metathesis reaction can be run under any desired pressure. In some instances, it may be desirable to maintain a total pressure that is high enough to keep the cross-metathesis reagent in solution. Therefore, as the molecular weight of the cross-metathesis reagent increases, the lower pressure range typically decreases since the boiling point of the cross-metathesis reagent increases. The total pressure may be selected to be greater than 0.1 atm (10 kPa), or greater than 0.3 atm (30 kPa), or greater than 1 atm (100 kPa). In some embodiments, the reaction pressure is no more than about 70 atm (7000 kPa), or no more than about 30 atm (3000 kPa). In some embodiments, the pressure for the metathesis reaction ranges from about 1 atm (100 kPa) to about 30 atm (3000 kPa).

In some embodiments, it may be desirable to treat the reactant composition (or one or more ingredients in the reactant composition) prior to carrying out the metathesis reaction, for example, to reduce the concentration of any catalyst poisons or other interfering species that may be present in the composition. Useful pre-treatment methods are described in United States Patent Application Publication No. 2011/0113679 and in PCT Publication Nos. WO 2014/139679 and WO 2014/160417, all three of which are hereby incorporated by reference as though fully set forth herein.

For example, in some embodiments, the materials in the reactant composition are subjected to metathesis reactions using the compounds disclosed herein are purified from impurities that may poison the catalytic effect of the compounds. Suitable methods include, but are not limited to, percolation through molecular sieves to remove water (or reduce water content to the acceptable level), optionally followed by a further percolation through activated alumina to remove/cleave organic peroxide and eliminate other impurities (e.g. alcohols, aldehydes, ketones). In some embodiments, distillation from sodium and/or potassium (e.g. styrene) may be sufficient to obtain suitably pure substrates. Similarly, when the water content is not high (e.g., less than about 250 ppm, relative to the concentration of the metathesis substrate material), percolation through alumina may be sufficient. A typical commercially-available alumina is SELEXSORB (BASF, Leverkusen, Germany). This is an activated alumina-based adsorbent containing a proprietary modifier, and is used as an industrial adsorbent.

In some other embodiments, materials in the reactant composition are used without purification, e.g., if trialkylaluminum (e.g. triethylaluminum) is added to the metathesis reaction. In such instances, trialkylaluminum may be used as an additive, e.g., in an amount of 0.5-5.0 mol %, relative to the concentration of the metathesis substrate material. Using this method or a combination of trialkylaluminum with molecular sieves and/or alumina may provide <10 ppm water content and, in some cases, the peroxide content is reduced, e.g., to below its detection limit.

Derivation from Natural Oils

In general, the compounds of formula (I) can be derived from natural oils and their derivatives. Such derivation can be carried out by any suitable means, including, but not limited to, metathesis of natural oils (e.g., by ethenolysis, propenolysis, butenolysis, etc.), fermentation, treatment by microorganisms, etc.

As noted above, olefin metathesis provides one possible means to convert certain natural oil feedstocks into olefinic compounds, such as compounds of formula (Ia) and, in some embodiments, compounds of formula (Ib). When fatty acids containing a carbon-carbon double bond undergo metathesis reactions in the presence of a metathesis catalyst, some or all of the original carbon-carbon double bonds are broken, and new carbon-carbon double bonds are formed. The products of such metathesis reactions include carbon-carbon double bonds in different locations, which can provide unsaturated organic compounds having useful chemical properties.

In some embodiments, after any optional pre-treatment of the natural oil feedstock, the natural oil feedstock is reacted in the presence of a metathesis catalyst in a metathesis reactor. In some other embodiments, an unsaturated ester (e.g., an unsaturated glyceride, such as an unsaturated triglyceride) is reacted in the presence of a metathesis catalyst in a metathesis reactor. These unsaturated esters may be a component of a natural oil feedstock, or may be derived from other sources, e.g., from esters generated in earlier-performed metathesis reactions. In certain embodiments, in the presence of a metathesis catalyst, the natural oil or unsaturated ester can undergo a self-metathesis reaction with itself. In other embodiments, the natural oil or unsaturated ester undergoes a cross-metathesis reaction with the low-molecular-weight olefin or mid-weight olefin. The self-metathesis and/or cross-metathesis reactions form a metathesized product wherein the metathesized product comprises olefins and esters.

In some embodiments, the low-molecular-weight olefin is in the $C_{2-6}$ range. As a non-limiting example, in one embodiment, the low-molecular-weight olefin may comprise at least one of: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. In some instances, a higher-molecular-weight olefin can also be used. Because the compounds of formula (Ia) and the compounds of formula (Ib) have terminal carbon-carbon double bonds, it can be desirable to use a short-chain alpha olefin, such as ethylene, propylene, or 1-butene.

In some embodiments, the metathesis comprises reacting a natural oil feedstock (or another unsaturated ester) in the presence of a metathesis catalyst. In some such embodiments, the metathesis comprises reacting one or more unsaturated glycerides (e.g., unsaturated triglycerides) in the natural oil feedstock in the presence of a metathesis catalyst. In some embodiments, the unsaturated glyceride comprises one or more esters of oleic acid, linoleic acid, linoleic acid, or combinations thereof. In some other embodiments, the unsaturated glyceride is the product of the partial hydrogenation and/or the metathesis of another unsaturated glyceride (as described above). In some such embodiments, the metathesis is a cross-metathesis of any of the aforementioned unsaturated triglyceride species with another olefin, e.g., an alkene. In some such embodiments, the alkene used in the cross-metathesis is a lower alkene, such as ethylene, propylene, 1-butene, 2-butene, etc. In some embodiments, the alkene is ethylene. In some other embodiments, the alkene is propylene. In some further embodiments, the alkene is 1-butene. And in some even further embodiments, the alkene is 2-butene.

Metathesis reactions can provide a variety of useful products, when employed in the methods disclosed herein. For example, terminal olefins and internal olefins may be derived from a natural oil feedstock, in addition to other valuable compositions. Moreover, in some embodiments, a number of valuable compositions can be targeted through the self-metathesis reaction of a natural oil feedstock, or the cross-metathesis reaction of the natural oil feedstock with a low-molecular-weight olefin or mid-weight olefin, in the presence of a metathesis catalyst. Such valuable compositions can include fuel compositions, detergents, surfactants, and other specialty chemicals. Additionally, transesterified products (i.e., the products formed from transesterifying an ester in the presence of an alcohol) may also be targeted, non-limiting examples of which include: fatty acid methyl esters ("FAMEs"); biodiesel; 9-decenoic acid ("9DA") esters, 9-undecenoic acid ("9UDA") esters, and/or 9-dodecenoic acid ("9DDA") esters; 9DA, 9UDA, and/or 9DDA; alkali metal salts and alkaline earth metal salts of 9DA, 9UDA, and/or 9DDA; dimers of the transesterified products; and mixtures thereof.

The compounds of formula (Ia) contain at least two carbon-carbon double bonds at the 1 and 4 positions. Such compounds can be readily derived from cross-metathesizing a polyunsaturated fatty acids or esters thereof (e.g., linoleic acid esters or linolenic acid esters). For example, cross-metathesizing a short-chain alpha-olefin with a linoleic acid ester (e.g., methyl linoleate or a glyceryl linoleate) can yield terminal olefinic compounds, such as 9,12-tridecadienoate esters (e.g., methyl or glyceryl), 1,4-decadiene, etc. In embodiments where the ester is a glyceryl ester, the glycerides can be transesterified using methanol, ethanol, and the like to make monohydric esters (e.g., methyl esters, ethyl esters, etc.). The same principles apply for compounds of formula (Ib).

As noted above, olefin metathesis of natural oils can be used to make one or more of the reactants used in the methods disclosed herein. Any suitable natural oil or natural oil derivative can be used. Examples of natural oils include, but are not limited to, vegetable oils, algae oils, fish oils, animal fats, tall oils, derivatives of these oils, combinations of any of these oils, and the like. Representative non-limiting examples of vegetable oils include rapeseed oil (canola oil), coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil. Representative non-limiting examples of animal fats include lard, tallow, poultry fat, yellow grease, and fish oil. Tall oils are by-products of wood pulp manufacture. In some embodiments, the natural oil or natural oil feedstock comprises one or more unsaturated glycerides (e.g., unsaturated triglycerides). In some such embodiments, the natural oil feedstock comprises at least 50% by weight, or at least 60% by weight, or at least 70% by weight, or at least 80% by weight, or at least 90% by weight, or at least 95% by weight, or at least 97% by weight, or at least 99% by weight of one or more unsaturated triglycerides, based on the total weight of the natural oil feedstock.

The natural oil may include canola or soybean oil, such as refined, bleached and deodorized soybean oil (i.e., RBD soybean oil). Soybean oil typically includes about 95 percent by weight (wt %) or greater (e.g., 99 wt % or greater) triglycerides of fatty acids. Major fatty acids in the polyol esters of soybean oil include but are not limited to saturated fatty acids such as palmitic acid (hexadecanoic acid) and stearic acid (octadecanoic acid), and unsaturated fatty acids such as oleic acid (9-octadecenoic acid), linoleic acid (9,12-octadecadienoic acid), and linolenic acid (9,12,15-octadecatrienoic acid).

Examples of metathesized natural oils include but are not limited to a metathesized vegetable oil, a metathesized algal oil, a metathesized animal fat, a metathesized tall oil, a metathesized derivatives of these oils, or mixtures thereof. For example, a metathesized vegetable oil may include metathesized canola oil, metathesized rapeseed oil, metathesized coconut oil, metathesized corn oil, metathesized cottonseed oil, metathesized olive oil, metathesized palm oil, metathesized peanut oil, metathesized safflower oil, metathesized sesame oil, metathesized soybean oil, metathesized sunflower oil, metathesized linseed oil, metathesized palm kernel oil, metathesized tung oil, metathesized jatropha oil, metathesized mustard oil, metathesized camelina oil, metathesized pennycress oil, metathesized castor oil, metathesized derivatives of these oils, or mixtures thereof. In another example, the metathesized natural oil may include a metathesized animal fat, such as metathesized lard, metathesized tallow, metathesized poultry fat, metathesized fish oil, metathesized derivatives of these oils, or mixtures thereof.

Such natural oils can contain esters, such as triglycerides, of various unsaturated fatty acids. The identity and concentration of such fatty acids varies depending on the oil source, and, in some cases, on the variety. In some embodiments, the natural oil comprises one or more esters of oleic acid, linoleic acid, linolenic acid, or any combination thereof. When such fatty acid esters are metathesized, new compounds are formed. For example, in embodiments where the metathesis uses certain short-chain olefins, e.g., ethylene, propylene, or 1-butene, and where the natural oil includes esters of oleic acid, an amount of 1-decene, among other products, is formed. Following transesterification, for example, with an alkyl alcohol, an amount of 9-denenoic acid methyl ester is formed. In some such embodiments, a separation step may occur between the metathesis and the transesterification, where the alkenes are separated from the esters. In some other embodiments, transesterification can occur before metathesis, and the metathesis is performed on the transesterified product.

The compounds of formula (Ia) and the compounds of formula (Ib) can include compounds having functional groups different from those typically found in natural oils, i.e., different from acids and esters. In such instances, those compounds can be formed via standard organic transformations known to those of skill in the art.

EXAMPLES

Example 1

Self-metathesis of Natural Oil Derived methyl 9,12-tridecadienoate or Soy-derived 1-decene/1,4-decadiene/1,4,7-decatriene Mixture In a nitrogen-filled glovebox, a glass vial was charged with 1 g of the olefin substrate, then a solution of catalyst in toluene (0.005-0.025 M) was added to the vial in one portion. The mixture was allowed to stir open to the glovebox atmosphere at ambient temperature or 30° C. by use of an aluminum heating block atop a magnetic hotplate stirrer. After two to four hours the reactions were quenched by removing the vials from the glovebox and exposing the mixtures to air. Reactions products were identified by GC-MS and conversion and selectivity were determined by GC-FID using calculated response factors. Results for these reactions are shown in Tables 1 and 2. "Conversion (%)" for the self-metathesis of methyl 9,12-tridecadienoate is given by the following equation:

$$\text{Conversion (\%)} = 100 \times \frac{2 \times \sum (\textit{Diester} \text{ Products adjusted area})}{\left[ \begin{array}{c} \sum (\text{Methyl 9,12-tridecadienoate adjusted area}) + \\ (2 \times \sum (\textit{Diester} \text{ Products adjusted area})) \end{array} \right]}$$

where the "Diester Products" are the following materials:

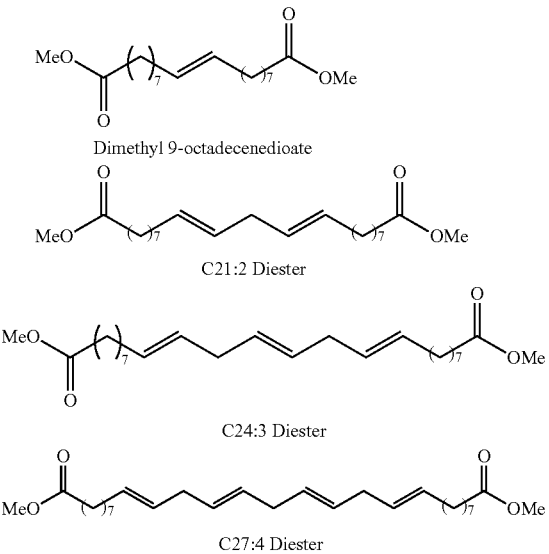

Dimethyl 9-octadecenedioate

C21:2 Diester

C24:3 Diester

C27:4 Diester

'Selectivity for C24:3 Diester (%)' for the self-metathesis of methyl 9,12-tridecadienoate is given by the following equation:

$$\text{Selectivity for } C24{:}3 \text{ Diester } (\%) = 100 \times \frac{C24{:}3 \text{ Diester adjusted area}}{\sum (\text{Diester Products adjusted area})}$$

Table 1 displays data collected for the self-metathesis of methyl 9,12-tridecadienoate with a moderate starting peroxide value of 12.75 mEq/kg which as treated with alumina to reduce this value to 0.06 mEq/kg.

TABLE 1

| Entry | Catalyst | Catalyst Loading (ppmwt) | Conversion (%) | Selectivity for C24:3 Diester (%) |
|---|---|---|---|---|
| 1 | 1 | 1325 | 81.1 | 51.4 |
| 2 | 1 | 331 | 9.4 | 100 |
| 3 | 1 | 662 | 62.5 | 76 |
| 4 | 2 | 1895 | 87.4 | 85 |
| 5 | 2 | 948 | 69.4 | 94.3 |
| 6 | 3 | 1228 | 38.4 | 88.2 |
| 7 | 3 | 614 | 22.0 | 92.5 |
| 8 | 3 | 474 | 30.0 | 98.2 |
| 9 | 3 | 190 | 2.9 | 100 |

Table 2 displays data collected for the self-metathesis of methyl 9,12-tridecadienoate with a high starting peroxide value of >100 mEq/kg. Due to the low quality of this material a multistep purification using previously identified methods (United States Patent Application No. 2014/0275595 A1) were required to generate the required substrate purity.

TABLE 2

| Entry | Catalyst | Catalyst Loading (ppmwt) | Conversion (%) | Selectivity for C24:3 Diester (%) |
|---|---|---|---|---|
| 1 | 1 | 1000 | 45.0 | 80.2 |
| 2 | 1 | 500 | 25.3 | 89.8 |
| 3 | 2 | 1000 | 77.7 | 81.7 |
| 4 | 2 | 500 | 63.1 | 92.3 |
| 5 | 4 | 1000 | 68.9 | 56.3 |
| 6 | 4 | 500 | 86.3 | 52.1 |
| 7 | 5 | 1000 | 24.8 | 86.1 |
| 8 | 5 | 500 | 13.0 | 91.5 |

'Conversion (%)' for the self-metathesis of soy-derived 1-decene/1,4-decadiene/1,4,7-decatriene mixture is given by the following equation:

$$\text{Conversion } (\%) = 100 \times \frac{2 \times \sum (C18 \text{ Olefins adjusted area})}{\sum \left[ \begin{array}{l} \left( \begin{array}{l} \text{1-decene, 1,4-decadiene, 1,4,7-decatriene} \\ \text{adjusted area} \end{array} \right) + \\ \left( 2 \times \sum \left( \begin{array}{l} C12, C15, C18, C21, C24, C27 \\ \text{and } C30 \text{ Olefins adjusted area} \end{array} \right) \right) \end{array} \right]}$$

where the "C12, C15, C18, C21, C24, C27 and C30 Products" are the following materials:

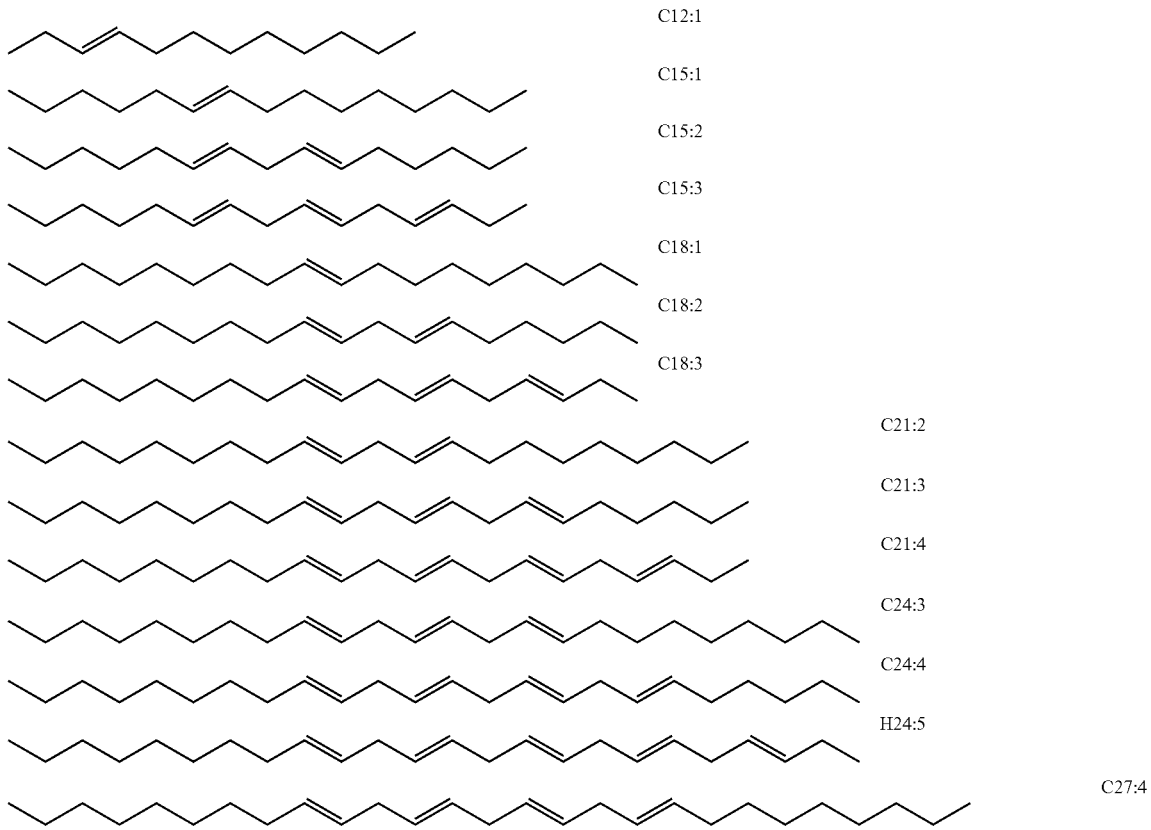

C12:1

C15:1

C15:2

C15:3

C18:1

C18:2

C18:3

C21:2

C21:3

C21:4

C24:3

C24:4

H24:5

C27:4

-continued

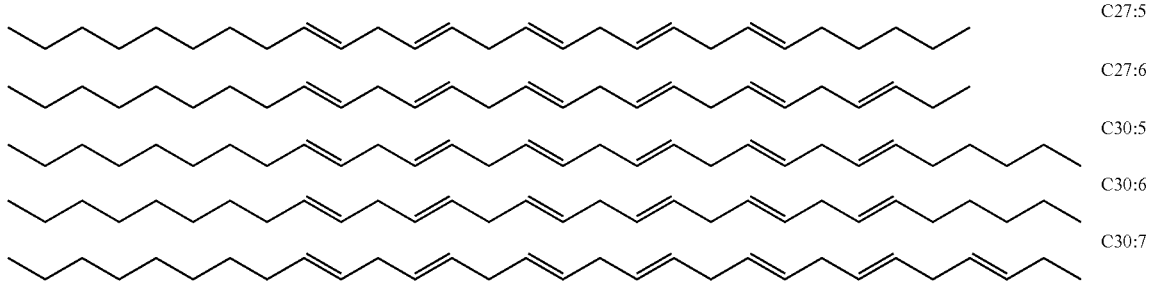

C27:5
C27:6
C30:5
C30:6
C30:7

'Selectivity for C18 Olefins (%)' for the self-metathesis of soy-derived 1-decene/1,4-decadiene/1,4,7-decatriene mixture is given by the following equation:

Selectivity for C18 Olefins (%) =
$$100 \times \frac{C18 \text{ Olefins adjusted area}}{\sum \begin{pmatrix} C12, C15, C18, C21, C24, C27 \\ \text{and } C30 \text{ Olefins adjusted area} \end{pmatrix}}$$

Soy-derived decenes were generated at Elevance Renewable Sciences, Inc. The composition of the material was found to be approximately 75% 1-decene, 3% isomerized decene, 13.5% 1,4-decadiene, 8.5% 1,4,7-decatriene. The material had a PV of 17.46 and a moisture content of 56.6 ppm. Alumina and molecular sieve pretreatment reduced the PV to <0.06 and moisture to <10 ppm. Screening results for the self-metathesis of soy decenes is shown in Table 3.

TABLE 3

| Entry | Catalyst | Catalyst Loading (ppmwt) | Conversion (%) | Selectivity for C18 Olefins (%) |
|---|---|---|---|---|
| 1 | 1 | 535 | 100.0 | 62.8 |
| 2 | 1 | 268 | 81.7 | 90.9 |
| 3 | 1 | 107 | 11.9 | 100 |
| 4 | 1 | 54 | 2.3 | 100 |

Example 2

Cross-metathesis of Natural Oil Derived methyl 9,12-tridecadienoate/methyl 9-decenoate Mixtures In a nitrogen-filled glovebox, two 9,12-tridecadienoate/methyl 9-decenoate mixtures were prepared either in a 1:1 or 2:1 molar ration. A glass vial was charged with 1 g of the olefin mixture, then a solution of catalyst in toluene (0.005-0.025 M) was added to the vial in one portion. The mixture was allowed to stir at 30° C. by use of an aluminum heating block atop a magnetic hotplate stirrer. After two to four hours the reactions were quenched by removing the vials from the glovebox and exposing the mixtures to air. Reactions products were identified by GC-MS and conversion and selectivity were determined by GC-FID using calculated response factors.

'Conversion (%)' for the cross-metathesis of methyl 9,12-tridecadienoate and methyl 9-decenoate is given by the following equation:

$$\text{Conversion (\%)} = 100 \times \frac{2 \times \sum (\textit{Diester} \text{ Products adjusted area})}{\left[ \sum \begin{pmatrix} \text{Methyl 9,12-Tridecadienoate and} \\ \text{Methyl 9-Decenoate adjusted area} \end{pmatrix} + \right.}$$
$$\left. (2 \times \sum (\textit{Diester} \text{ Products adjusted area})) \right]$$

where the 'Diester Products' are the following materials:

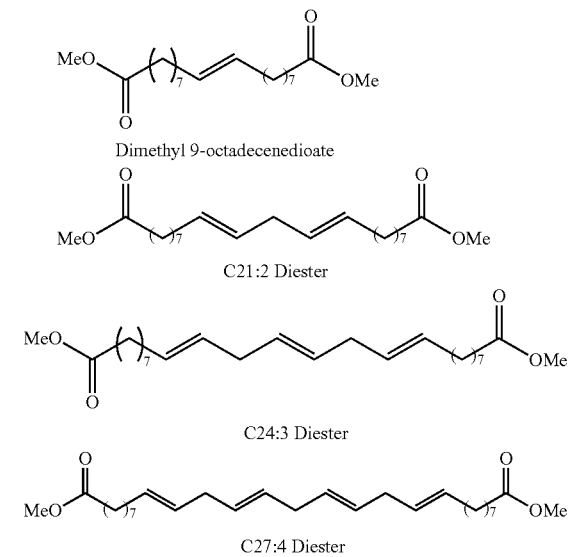

Dimethyl 9-octadecenedioate

C21:2 Diester

C24:3 Diester

C27:4 Diester

'Selectivity for C21:3 Diester (%)' for the self-metathesis of methyl 9,12-tridecadienoate is given by the following equation:

Selectivity for C24:3 Diester (%) =
$$100 \times \frac{C21:2 \textit{ Diester} \text{ adjusted area}}{\sum (\textit{Diester} \text{ Products adjusted area})}$$

TABLE 4

| Entry | Catalyst | Catalyst Loading (ppmwt) | Methyl 9,12-tridecadienoate-to-methyl 9-decenoate molar ratio | Conversion (%) | Selectivity for C21:2 Diester (%) |
|---|---|---|---|---|---|
| 1 | 2 | 750 | 1:1 | 55.5 | 52.2 |
| 2 | 2 | 500 | 1:1 | 44.4 | 52.4 |

TABLE 4-continued

| Entry | Catalyst | Catalyst Loading (ppmwt) | Methyl 9,12-tridecadienoate-to-methyl 9-decenoate molar ratio | Conversion (%) | Selectivity for C21:2 Diester (%) |
|---|---|---|---|---|---|
| 3 | 2 | 250 | 1:1 | 27.8 | 52.2 |
| 4 | 2 | 750 | 2:1 | 58.0 | 44.6 |
| 5 | 2 | 500 | 2:1 | 46.8 | 44.1 |
| 6 | 2 | 250 | 2:1 | 29.0 | 44.1 |
| 7 | 4 | 750 | 1:1 | 74.5 | 41.5 |
| 8 | 4 | 500 | 1:1 | 68.8 | 45.4 |
| 9 | 4 | 250 | 1:1 | 52.3 | 49.4 |
| 10 | 4 | 750 | 2:1 | 83.9 | 43.7 |
| 11 | 4 | 500 | 2:1 | 76.7 | 46.2 |
| 12 | 4 | 250 | 2:1 | 58.2 | 47.6 |

Catalysts Structures.

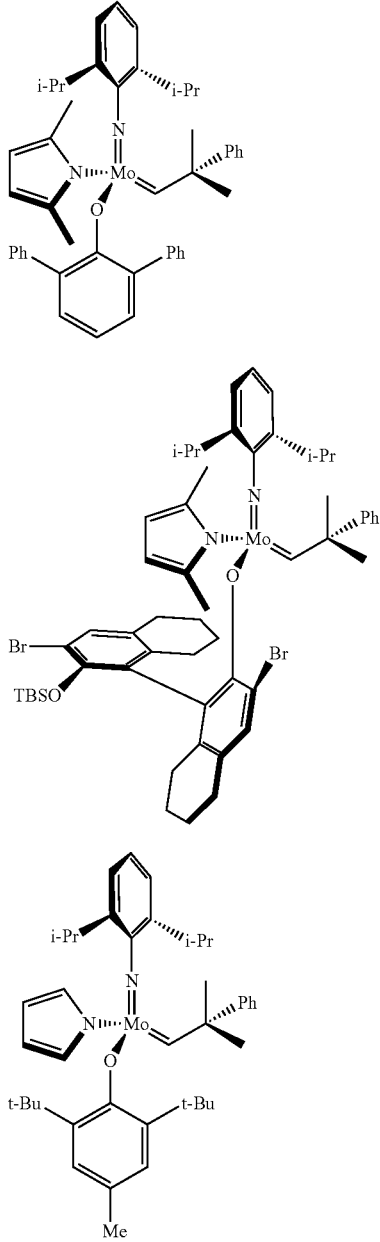

1

2

3

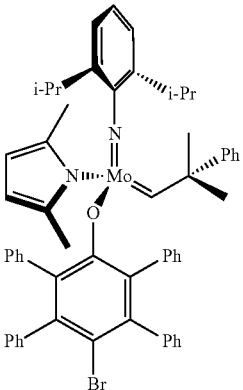

4

5

GC-MS analytical method for identification of products. The GC-MS analyses were run using an Agilent 7890 A instrument equipped with a 5975C mass spectrometer and the following conditions:
  Column: Restek Rtx-65TG (65% diphenylsiloxane, 35% dimethylsiloxane); 30 m×250 μm (I.D.)×0.1 μm film thickness.
  Injector temperature: 275° C.
  Split Ratio: 20:1
  Oven Temperature Program: starting temperature of 40° C., hold time of five minutes, ramp rate of 20° C./min to 370° C., hold time of 11.5 minutes
  Carrier Gas: Helium
  Flow Rate: 2 mL/min GC-FID analytical method for determination of conversion and selectivity. The GC-FID analyses were run using an Agilent 6850 instrument and the following conditions:
  Column: Restek Rxi-17Sil MS (50% diphenylsiloxane, 50% dimethylsiloxane); 30 m×250 μm (I.D.)×0.25 μm film thickness.
  Injector temperature: 275° C.
  Split Ratio: 100:1
  Oven Temperature Program: starting temperature of 100° C., hold time of one minute, ramp rate of 25° C./min to 325° C., with no final hold time.
  Carrier Gas: Hydrogen
  Flow Rate: 1 mL/min

What is claimed is:
1. A method for forming a dimer by olefin metathesis, the method comprising:
  providing a reactant composition comprising a terminally unsaturated diene, which is methyl 9,12-tridecadienoate; and self-metathesizing the terminally unsaturated diene, methyl 9,12-tridecadienoate, in the presence of a metathesis catalyst at the terminal double bond of the terminally unsaturated diene to form a product composition comprising 1,24-dimethyl 9,12,15-tetracosatriendioate;

provided that the terminally unsaturated diene, methyl 9,12-tridecadienoate, is derived from a natural oil.

2. The method of claim 1, comprising hydrogenating the 1,24-dimethyl 9,12,15-tetracosatriendioate to form 1,24-dimethyl tetracosanedioate.

3. The method of claim 2, comprising converting the 1,24-dimethyl tetracosanedioate to form 1,24-tetracosanedioic acid.

4. The method of claim 3, wherein the converting comprises hydrolysis.

5. The method of claim 3, wherein the converting comprises saponification followed by acidification.

6. A method for forming a dimer by olefin metathesis, the method comprising:

providing a reactant composition comprising a terminally unsaturated diene, which is methyl 9,12-tridecadienoate, and methyl 9-decenoate; and cross-metathesizing the terminally unsaturated diene, methyl 9,12-tridecadienoate, and the methyl 9-decenoate in the presence of a metathesis catalyst at the terminal double bond of the terminally unsaturated diene to form a product composition comprising 1,21-dimethyl 9,12-heneicosadiendioate;

provided that the terminally unsaturated diene, methyl 9,12-tridecadienoate, or the methyl 9-decenoate is derived from a natural oil.

7. The method of claim 6, comprising hydrogenating the 1,21-dimethyl 9,12-heneicosadiendioate to form 1,21-dimethyl heneicosanedioate.

8. The method of claim 7, comprising converting the 1,21-dimethyl heneicosanedioate to form 1,21-heneicosanedioic acid.

9. The method of claim 8, wherein the converting comprises hydrolysis.

10. The method of claim 8, wherein the converting comprises saponification followed by acidification.

* * * * *